United States Patent [19]

Rangaswamy

[11] Patent Number: 4,512,768

[45] Date of Patent: Apr. 23, 1985

[54] ANALGESIC SYRINGE

[76] Inventor: Avvari Rangaswamy, Stevens Hospital, Welch, W. Va. 24801

[21] Appl. No.: 466,535

[22] Filed: Feb. 15, 1983

Related U.S. Application Data

[63] Continuation-in-part of Ser. No. 417,188, Sep. 10, 1982, abandoned.

[51] Int. Cl.³ .............................................. A61M 5/00
[52] U.S. Cl. ..................................... 604/191; 604/272
[58] Field of Search ...................... 604/88, 89, 90, 190, 604/191, 164, 272

[56] References Cited

U.S. PATENT DOCUMENTS

| | | | |
|---|---|---|---|
| 2,564,977 | 8/1951 | Hsihu | 604/272 |
| 3,530,492 | 9/1970 | Ferber . | |
| 3,547,119 | 12/1970 | Hall et al. | 604/164 |
| 3,749,084 | 7/1973 | Cucchiara | 604/191 |
| 4,040,420 | 8/1977 | Speer . | |
| 4,306,554 | 12/1981 | Schwartz et al. | 604/190 |

FOREIGN PATENT DOCUMENTS 1142769  9/1957  France ............................... 604/272

Primary Examiner—John D. Yasko
Attorney, Agent, or Firm—Memel, Jacobs, Pierno & Gersh

[57] ABSTRACT

A syringe article, for analgesic puncture with twin needles, the syringe containing a thin walled plastic reservoir filled with local anesthetic mounted under a collapsible roof and located at the distal end of the syringe barrel adjacent the twin needles, so that depression of the syringe plunger compresses sharp projections against the reservoir which is then ruptured to release the local anesthetic for injection into the flesh which will be punctured, the local anesthetic being passed through pores in the wall of an outer positioned needle into the patient's flesh.

5 Claims, 5 Drawing Figures

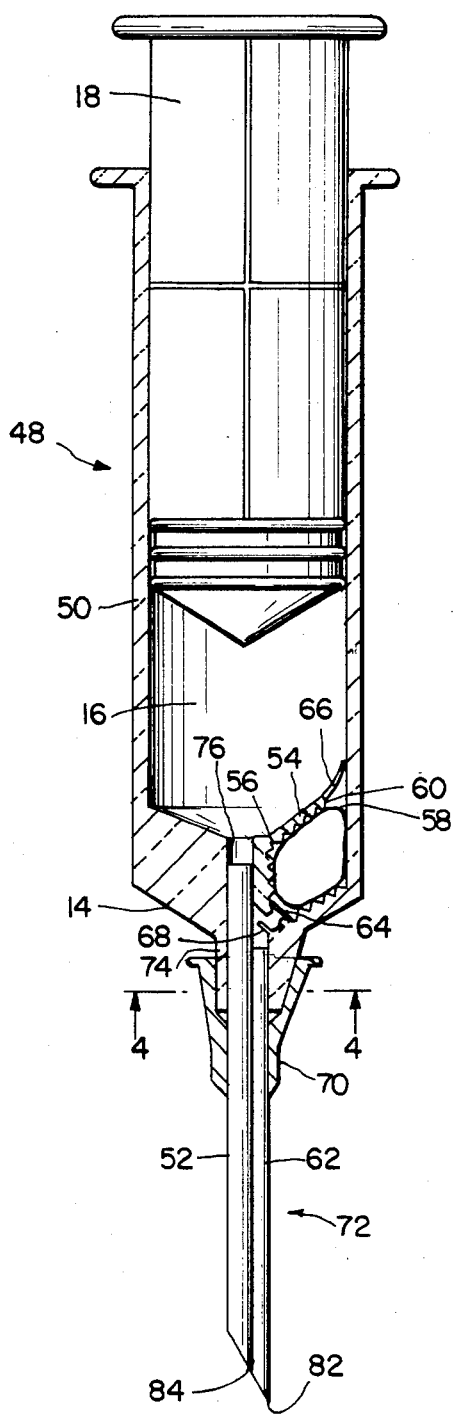
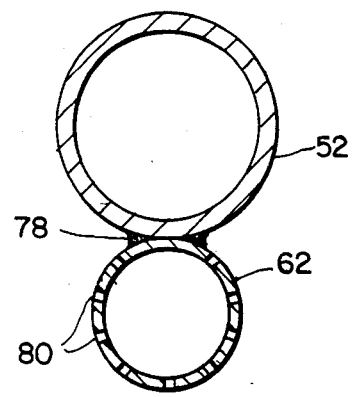
FIG. 5
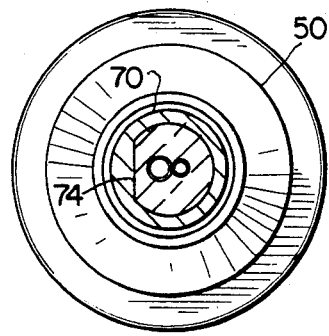
FIG. 3              FIG. 4

ANALGESIC SYRINGE

BACKGROUND OF THE INVENTION

This application is a continuation-in-part of application Ser. No. 417,188 of Avvari Rangaswamy filed Sept. 10, 1982 now abandoned.

This invention relates to syringes for painlessly performing a venipuncture or similar puncture type procedure, and, more particularly, to syringes which provide for multi-directional initial injection of a local anesthetic so as to allow for painless passage of a needle into a patient.

Various syringe types are known in the art which provide for multi-medication injections. In general, these syringes incorporate moveable seals in the cylinder of the syringe so that various pharmaceutical substances can be separately contained in the syringe for serial injection. As the plungers of such syringes are depressed into the syringe cylinders the moveable seals advance the various preloaded pharmaceuticals toward the syringe needle. The succeeding pharmaceuticals, after the first is passed through the syringe needle, are fed into the needle by having an extension of the needle, into the cavity of the syringe cylinder, pierce through the moveable seals as they are advanced by the plunger. However, because the pharmaceuticals only pass into the patient through a single exit located at end of needle, all such known multi-medication syringe types are incapable of providing effective precursor local anesthetization for the passage of the syringe needle into a patient.

SUMMARY OF THE INVENTION

Venipuncture is one of the more commonly performed medical procedures. Such surgical puncture of a vein to either withdraw fluid or insert a needle, with or without a soft intravenous catheter, to administer intravenous fluids can be a difficult and painful procedure for many patients—especially for children or the frequently hospitalized patients in whom it can be difficult to insert a large bore needle into a vein. The present invention minimizes the discomfort associated with such procedures, and is particularly useful in treating children and patients in whom it is hard to find a moderate size vein.

This invention consists of a syringe with a thin walled plastic reservoir lodged under a collapsible roof that is located at the distal end of the syringe barrel adjacent the needle. Hermetically stored in the thin walled reservoir is a local anesthetic. Depression of the syringe plunger applies pressure to the collapsible roof which compresses sharp projections through the walls of the plastic reservoir. The sharp projections rupture the plastic reservoir, and the continued depression of the plunger induces flow of the anesthetic through a filter and one way valve into a porous needle. The porous needle projects forward of a second needle. This second needle is coupled to the syringe cylinder for passage of fluids. The openings along the length of the porous needle provide for flow of the local anesthetic in multiple directions which results in anesthetization of the region through which the needles are passed in search of a vein or body cavity.

BRIEF DESCRIPTION OF THE DRAWINGS

In the drawings:

FIG. 3 is a partial cross section of a syringe with a paired needle structure according to the present invention;

FIG. 4 is a cross section of the distal end of the syringe illustrated in FIG. 3 showing how the paired needle structure is registered to fit into the syringe barrel; and, FIG. 5 is a further cross section of the paired needle structure illustrated in FIG. 3.

DETAILED DESCRIPTION OF THE INVENTION

Figure 1:
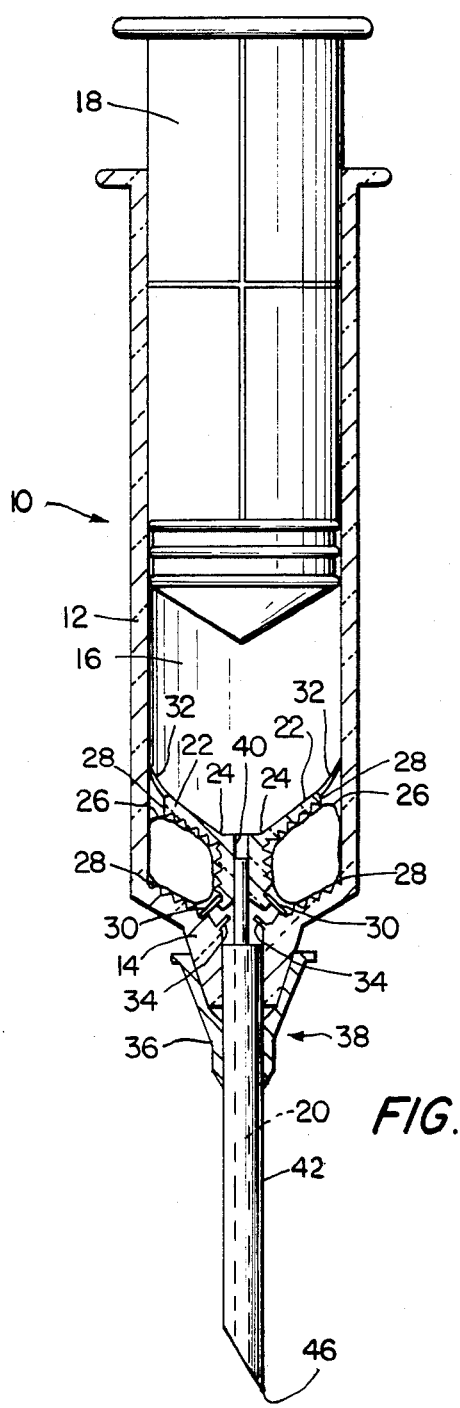
FIG. 1 is a partial cross section of a syringe with an aqueduct needle according to the present invention.

Referring now to the drawings, wherein corresponding components are designated by the same reference numerals throughout the various figures, a syringe according to the invention is illustrated in FIG. 1 and generally designated by reference numeral 10. Syringe 10 includes a syringe barrel 12 having a distal end 14. The syringe barrel 12 is fabricated of plastic. Within the syringe barrel 12 is a cylinder 16 into which can be inserted a plunger 18 for evacuating the hollow cylinder 16 through a continuous walled cannula 20.

At the distal end 14 of the syringe barrel 12 is an annular collapsible roof 22. The annular collapsible roof 22 is attached to the syringe barrel 12 by a flexible section 24 providing a hinge for the annular collapsible roof 22. Lodged within the distal end 14 of the syringe barrel 12 under the collapsible roof 22 is an annular thin walled plastic reservoir 26 which contains a local anesthetic. The local anesthetic is released from the reservoir 26, which is ruptured, when the annular collapsible roof 22 compresses sharp plastic projections 28 into the reservoir 26. After release from the reservoir 26 the local anesthetic flows through annular filter 30, which prevents plastic material from ruptured reservoir 26 passing into porous needle 42. Such a flow path for the local anesthetic is preferred because flow back into the hollow cylinder 16 is inhibited by the annular collapsible roof 22 with its continuous hinge 24 and pliable annular seal 32. After passage through the annular filter 30 the local anesthetic passes through an annular one way valve consisting of a flexibly hinged plastic seal 34 which is open when fluid pressure is applied as a result of the local anesthetic being released from the plastic reservoir 26. The hinged plastic seal 34 closes the one way valve when the ambient pressure on the opposite side of the hinged plastic seal 34 from the plastic reservoir 26 is greater than that produced by the annular collapsible roof 22 compressing the reservoir 26. Such closing of the one way valve by hinged plastic seal 34 prevents fluids from backing up into the plastic reservoir 26 region. An example of when such backing up of fluid could occur is when fluid is being withdrawn from a patient by syringe 10.

Figure 2:
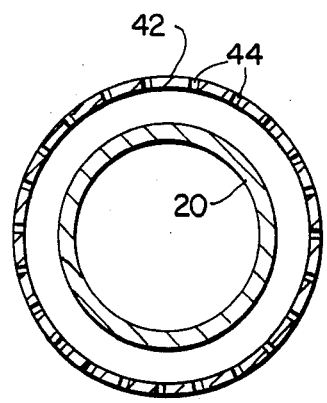
FIG. 2 is a further cross section of the aqueduct needle illustrated in FIG. 1.

Affixed at the distal end 14 of syringe 10 by a hub 36 is an aqueduct needle 38. Tube 40 within the distal end 14 of syringe 10 provides a sealing fit for the continuous walled cannula 20 so that fluids can be either passed to or from hollow cylinder •16 through the continuous walled cannula 20 which has openings at both ends. Annularly surrounding continuous walled cannula 20 is a porous needle 42 which has pores 44 around (See FIG. 2) and substantially along its entire length from hub 36 to its end 46. These pores 44 are closely and substantially uniformly spaced on the exterior wall of needle 42 so as to provide for uniform infusion of the local anesthetic from plastic reservoir 26 into the patient along the entire length of the aqueduct needle 38 which is inserted, and not just the end 46. Such uniform infusion assures effective anesthization for painless insertion of the aqueduct needle.

Another exemplary embodiment of the invention is shown in FIG. 3. Here syringe 48 includes a syringe barrel 50 having a distal end 14. The syringe barrel 50 is fabricated of plastic. Within the syringe barrel 50 is a hollow cylinder 16 into which can be inserted a plunger 18 for evacuation of the hollow cylinder 16 through a needle 52.

At the distal end 14 of the syringe barrel 50 is a collapsible roof 54. The collapsible roof 54 is attached to the syringe barrel 50 by a flexible section 56 providing a hinge for the collapsible roof 54. Lodged within the distal end 14 of the syringe barrel 50 under the collapsible roof 54 is a thin walled plastic reservoir 58 which contains a local anesthetic. The local anesthetic is released from the plastic reservoir 58, which is ruptured, when the collapsible roof 54 compresses sharp plastic projections 60 into the reservoir 58. After release from the reservoir 58 the local anesthetic flows through filter 64, which prevents plastic material from ruptured reservoir 58 passing into porous needle 62. Such a flow path for the local anesthetic is preferred because flow back into the hollow cylinder 16 is inhibited by the collapsible roof 54 with its continuous flexible hinge 56 and pliable seal 66. After passage through the filter 64 the local anesthetic passes through a one way valve consisting of a flexible hinged plastic seal 68 which is open when fluid pressure is applied as a result of the local anesthetic being released from the plastic reservoir 58. The hinged plastic seal 68 closes the one way valve when the ambient pressure on the opposite side of the hinged plastic seal 68 from the plastic reservoir 58 is greater than that produced by the collapsible roof 54 compressing the reservoir 58. Such closing of the one way valve by hinged plastic seal 68 prevents fluids from backing up into the plastic reservoir 58 region.

Affixed at the distal end 14 of syringe 48 by a hub 70 is a paired needle structure 72. Hub 70 is keyed for fitting onto syringe barrel 50 so that both needle 52 and porous needle 62 are rotationally properly aligned with syringe barrel 50. This registration of both needle 52 and porous needle 62 is accomplished by having a flat registration section 74 oriented with respect to both syringe barrel 50 and hub 70 that the paired needle structure 72 is properly aligned.

Tube 76 within the distal end 14 of syringe 48 provides a sealing fit for needle 52 so that fluids can be either passed to or from hollow cylinder 16 through needle 52. Abutting needle 52 and firmly affixed to it by a joint 78 is the narrow gauge (25–28G) porous needle 62. The narrow gauge porous needle 62 has pores 80 around (see FIG. 5) and substantially along its entire length from hub 70 to its end 82. These pores 80 are closely and substantially uniformly spaced on the exterior of porous needle 62 so as to provide for uniform infusion of the local anesthetic from plastic reservoir 58 into the patient along the entire length of the porous needle 62 which is inserted and not just the end 82. To further assure effective anesthization for painless insertion of the paired needle structure the narow gauge porous needle extends in front of the end 84 of needle 52 by 1/16th to 1/8th inch.

The above discussion and related illustrations of the present invention are directed primarily to preferred embodiments and practices of the invention. However, it is believed that numerous changes and modifications in the actual implementation of the concepts described herein will be apparent to those skilled in the art, and it is contemplated that such changes and modifications may be made without departing from the scope of the invention as defined by the following claims.

What is claimed is:

1. A syringe, comprising: means for releasing a first pharmaceutical into a porous needle as said porous needle is being inserted in a patient, and said porous needle being in fixed adjacent proximity with a continuous walled cannula or needle through which (1) a second pharmaceutical can be passed or (2) fluids can be withdrawn from the patient;

whereby said first pharmaceutical is infused substantially uniformly into the patient along the length of the inserted porous needle and therefore into the region which said continuous walled cannula or needle is passed.

2. A syringe as set forth in claim 1 in which said continuous walled cannula or needle is contained within said porous needle so that a fluid can be dispensed through the end and pores of said porous needle, and a separate fluid can be dispensed through the end of said continuous walled cannula or needle, or fluids can be withdrawn from the patient.

3. A syringe as set forth in claim 1 in which said continuous walled cannula or needle is abuttingly fixed longitudinally to said porous needle so that a fluid can be dispensed through the end and pores of said porous needle, and a separate fluid can be dispensed, or fluids can be withdrawn from the patient, through the end of said continuous walled cannula or needle.

4. A syringe as set forth in claim 1 in which said first pharmaceutical is contained in a hermetically sealed reservoir, which reservoir can be ruptured by means activated by depressing the syringe plunger so that said first pharmaceutical flows into said porous needle.

5. A syringe as set forth in claim 4 in which said first pharmaceutical flows from said ruptured reservoir through a filter and one way valve prior to entering said porous needle.

* * * * *